Figure 1:
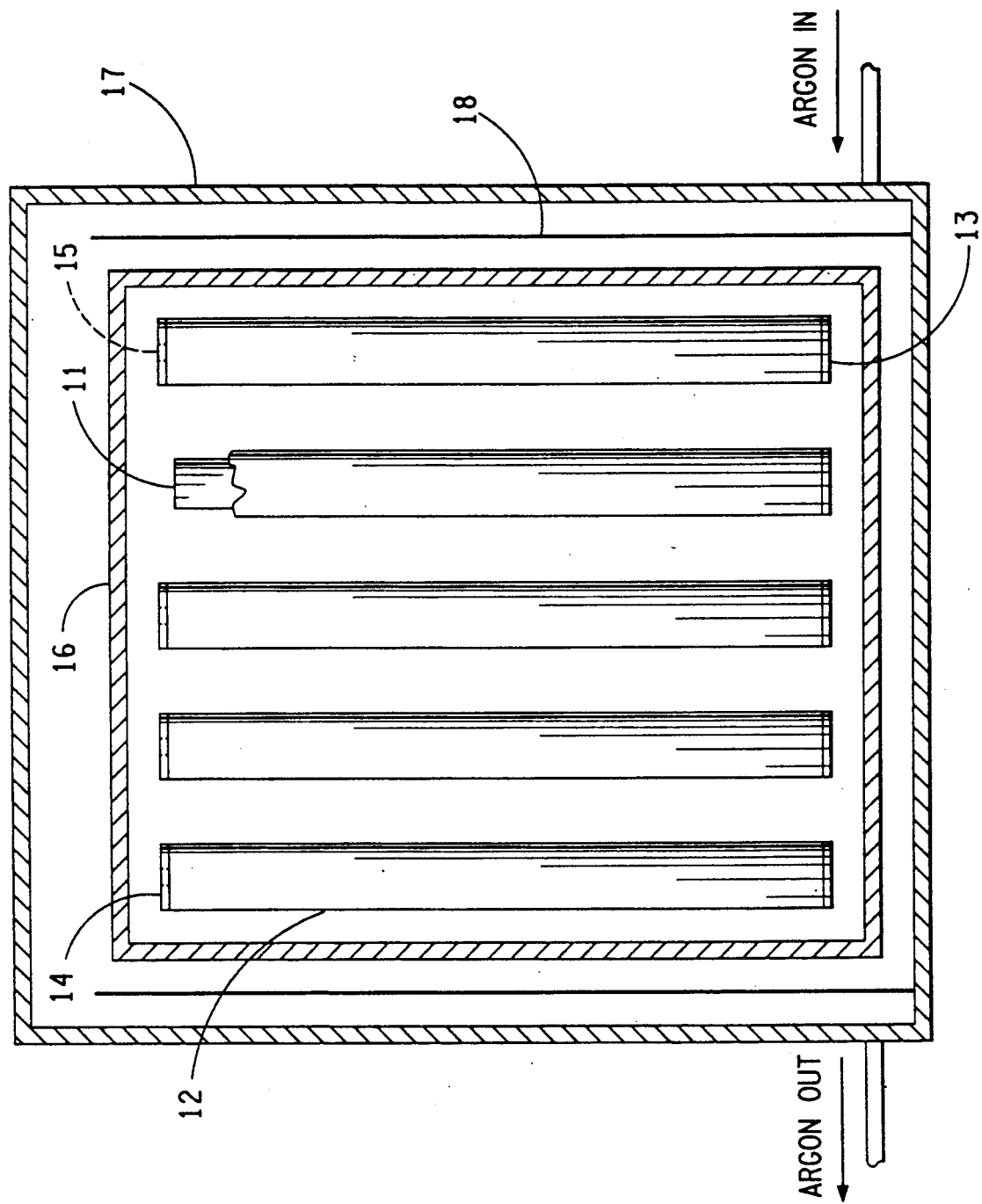

United States Patent [19]

Li et al.

[11] Patent Number: 5,037,928
[45] Date of Patent: Aug. 6, 1991

[54] PROCESS OF MANUFACTURING ULTRAHIGH MOLECULAR WEIGHT LINEAR POLYETHYLENE SHAPED ARTICLES

[75] Inventors: Stephen Li, Wilmington; Edward G. Howard, Jr., Hockessin, both of Del.

[73] Assignee: E. I. Du Pont de Nemours and Company, Wilmington, Del.

[21] Appl. No.: 500,053

[22] Filed: Mar. 23, 1990

Related U.S. Application Data

[63] Continuation-in-part of Ser. No. 426,918, Oct. 24, 1989, abandoned, which is a continuation-in-part of Ser. No. 288,576, Dec. 22, 1988, abandoned, which is a continuation-in-part of Ser. No. 278,912, Dec. 2, 1988.

[51] Int. Cl.$^5$ .................. B29C 43/12; C08F 110/02; A61F 2/32
[52] U.S. Cl. ........................ 526/352; 528/481; 528/483; 528/502; 528/503; 264/85; 264/126; 264/322; 264/331.17; 264/348; 264/313; 623/22; 425/405.2
[58] Field of Search ................ 264/85, 331.17, 235, 264/345, 346, 570, 319, 320, 126, 348, 322, 313; 526/352; 425/405.1, 405.2; 528/502, 481, 483, 499, 503; 623/18, 22

[56] References Cited

U.S. PATENT DOCUMENTS

| | | | |
|---|---|---|---|
| 3,576,933 | 4/1971 | Bates et al. | 264/570 |
| 3,944,536 | 3/1976 | Lupton et al. | 264/331 |
| 3,998,994 | 12/1976 | Decroix et al. | 264/345 |
| 4,217,087 | 8/1980 | Bowles | 425/405.2 |
| 4,348,350 | 9/1982 | Meier et al. | 264/570 |
| 4,587,163 | 5/1986 | Zachariades | 428/292 |

FOREIGN PATENT DOCUMENTS 1015338 12/1965 United Kingdom ............. 264/85

OTHER PUBLICATIONS

Lupton et al., Physical Properties of Extended Chain High Density Polyethylene; 1974; Jre Applied Polymer Sci; 18; 2407–2425.
Eyerer et al., Kunstuffe German Plastics 77 (1987), "Ultrahigh Molecular Polyethylene for Replacement Joints", pp. 617–622.
E. I. Du Pont de Nemours and company, DePuy, 1989, "A New Enhanced Ultra High Molecular Weight Polyethylene for Orthopaedic Applications: a Techanical Brief".
Eyerer et al., ANTEC '86, "Material Improvements of UHMWPE", pp. 1097–1100 (1986).
Bassett et al., "On Chain-Extended and Chain Folded Crystallization of Polyethylene", pp. 235–307 (1973), Phil. Mag., 29(2).
Bassett et al., "Oriented Chain-Extended Polyethylene", pp. 535–545 (1973).
Yasuniwa et al., Polymer Journal, 19 (7), 805 (1987).
Yasuniwa et al., Polymer Journal, 20(12), 1075 (1988).
Sawada et al., Polymer Journal, 11(7), 551 (1979).
Zachariades et al., Polymer Engineering and Science, vol. 526, 658–661 (1986).
Zachariades, Journal of Applied Polymer Science, vol. 32, 4277–4279 (1986).
Zachariades, Polymer Engineering and Science, vol. 25, No. 12, 747–750 (1985).

Primary Examiner—Jeffery Thurlow
Assistant Examiner—Mathieu Vargot
Attorney, Agent, or Firm—Linda Axamethy Floyd

[57] ABSTRACT

A process for preparing an ultrahigh molecular weight linear polyethylene (UHMWLPE) exhibiting a combination of properties including a creep resistance of less than 1% demonstrated under exposure to a temperature of 23° C. (+ or −1° C.) and a relative humidity of 50 (+ or −2% for 24 hours under a compression of 1000 psi) without sacrificing excellent tensile and flexural properties. The invention includes the use of an inert gas and a prescribed pattern of heating and cooling including a further heat and cooling treatment to create the superior properties of the UHMWLPE. Also included is the product of the process invention.

26 Claims, 1 Drawing Sheet

PROCESS OF MANUFACTURING ULTRAHIGH MOLECULAR WEIGHT LINEAR POLYETHYLENE SHAPED ARTICLES

CROSS-REFERENCE TO RELATED APPLICATION

This application is a continuation-in-part of my co-pending application U.S. Ser. No. 07/426,918 filed Oct. 24, 1989, now abandoned, which in turn is a continuation-in-part of U.S. Ser. No. 07/288,576 filed Dec. 22, 1988, now abandoned, which in turn is a continuation-in-part of my co-pending application U.S. Ser. No. 07/278,912 filed Dec. 2, 1988, now abandoned.

BACKGROUND OF THE INVENTION

1. Field of the Invention

This invention relates to a novel process for making ultrahigh molecular weight linear polyethylene (UHMWLPE). This novel UHMWLPE, in the form of a shaped article, exhibits a unique combination of properties making the material useful as a bearing surface, in general, but particularly useful as a prosthetic hip joint cup and as other prosthetic shapes for replacement of other joints of the human body. This article is the subject of copending U.S. Ser. No. 07/426,916 filed on Oct. 24, 1989 which is a continuation-in-part of co-pending U.S. Ser. No. 07/288,576 filed Dec. 22, 1988, which in turn is a continuation-in-part of co-pending U.S. Ser. No. 07/278,913, filed Dec. 2, 1988.

2. Description of the Prior Art

In U.S. Pat. No. 3,944,536 (March 1976), Lupton et al describe UHMWPE in the form of a fabricated article exhibiting an elastic modulus of 340,000 to 500,000 psi, a tensile impact strength of 140 to 600 ft lb/in$^2$, a density of 0.95 to 0.98 g/cc at 25° C., a crystalline melting point of 142 to 148° C. (as measured by differential thermal analysis) and a unique crystalline form characterized by the absence of fold spacings of 50-2000 Angstrom units (Å) and the presence of crystal spacings of about 10,000 Å. The critical feature of the process of producing this UHMWPE is disclosed to involve inducing crystallization of the molten polymer above 150° C. by rapidly increasing the applied pressure from an initial level of 1 to 1000 atmospheres to a second level of 2000 to 7000 atmospheres and then cooling rapidly while maintaining a pressure sufficient to maintain the polyethylene in the solid phase until the temperature is below the crystalline melting point of the polyethylene at atmospheric pressure.

In Kunstuffe German Plastics 77 (1987) pp. 617-622, in an article entitled "Ultrahigh Molecular Polyethylene for Replacement Joints", Eyrer et al. point out that the service life of joint replacements made of UHMWPE is limited. Analysis of the damage to over 250 explanted hip cups and tibial plateaus revealed a changed property profile which they explained by post-crystallization resulting from oxidative chain decomposition. They suggested optimizing the processing of polyethylene under higher pressure and higher temperature to increase the degree of crystallinity. The Eyrer et al. product displays a creep of above 5% at a compression of 1000 psi (6.9 N/mm$^2$) for 24 hours at 37° C.

One of the most remarkable advances in the medical field in recent years is the development of prosthetic joints, particularly the load bearing hip. The crippled and sometimes bed ridden elderly can walk again. The key to this development is UHMWPE because, not only does it have the necessary impact strength, but it initiates no adverse blood reactions. But at present, these prosthetic joints are limited to the older, less active segment of the population because the polymer tends to creep under the pressure that a younger more active person might develop while involved in recreation or employment. The creep would cause the loss of the desired tolerance required between the plastic socket and the polished metal ball attached to the femur. These changes in dimensions disturb the distribution of walking forces which in turn accelerates more creep and wear. Eventually the increased pain requires a traumatic revision operation. One objective of this invention is to provide a process for making UHMWPE prosthetic joints with improved creep resistance hence removing some of the age restriction existing with regard to the present polyethylene joints.

SUMMARY OF THE INVENTION

The object of this invention is to provide a process for making a tough UHMWLPE composition and articles that display a creep resistance, when exposed to a temperature of 23±1° C. and a relative humidity of 50±2% for 24 hours under a compression of 1000 psi, of less than 1% without sacrificing excellent tensile and flexural properties.

Specifically, the product obtained is a shaped UHMWLPE article exhibiting an elastic or flexural modulus of 250,000-500,000 psi, a tensile stress at yield of 3500-4500 psi, a tensile stress at break of 4000-9000 psi, a tensile modulus of 250,000-700,000 psi, an elongation of 200-500%, a notched Izod impact resistance of 12-25 ft. lb. per in. of notch, a creep at a compression of 1000 psi of less than 1% after 24 hours at a temperature of 23° C. and a relative humidity of 50%, the polyethylene having a molecular weight of 400,000-10,000,000 (the molecular chain length between folds being greater than 3500 Å), a single crystalline melting point of greater than 144° C. (as measured by differential scanning calorimetry) the reduction in said melting point upon remelting being greater than 11° C. and an infrared crystallinity index of at least about 0.45.

The process for obtaining the shaped article of this invention involves six (6) important steps:

1. forming, by milling or casting or the like the article from UHMWLPE having a molecular weight of 400,000-10,000,000, preferably at least 1,000,000 and most preferably at least 6,000,000;

2. surrounding the article with an inert material that is collapsible and impermeable; and placing the surrounded article in a pressure vessel containing a gaseous fluid, preferably argon;

3. heating the vessel to a temperature of at least 190° C. but no greater than 300° C., preferably 200° C.-230° C., and raising the pressure in the vessel to at least 280 MPa, preferably at least 300 MPa;

4. maintaining the temperature and pressure substantially as selected in step 3 for at least 0.5 hour, preferably at least one hour;

5. thereafter, cooling by reducing the temperature to a temperature at least below about 160° C.-170° C. preferably to 160° C. or below, most preferably below 140° C., while maintaining a pressure of at least 280 MPa preferably at least 300 MPa, at a slow rate, the rate of cooling being such that temperature gradients in the shaped article are substantially avoided. The polymer must be cooled slowly at the high pressure until it is fully crystallized. At 300 MPa pressure, the crystallization temperature of UHMWLPE of over one million molecular weight is in the range of 170° C.-190° C. The pressurized vessel should be cooled slowly to insure that the temperature of the polymer is not significantly above the vessel temperature, particularly if the pressure vessel construction does not permit means for measuring the temperature of the polymer itself; and 6. cooling and releasing the pressure on the shaped article in a manner such that any remelting of the article is prevented. This is accomplished by cooling at least to a temperature below the atmospheric pressure melting point, i.e., about 130° C.-135° C. preferably below 120° C., most preferably below 100° C. and releasing the pressure to reduce it from at least 280 MPa to approximately 100 kPa, either sequentially or simultaneously. It should be understood that it is necessary to cool the polymer to a temperature below its melting point at any particular pressure to insure that none of the polymer melts as the pressure is reduced since lowering the pressure lowers the melting point.

It has been found necessary to protect the surface of the article by enclosing it in a thin can during the process.

A very important step is the fifth step, i.e. cooling in a manner that limits severe temperature gradients in the article. For example, for a 1 inch × 6 inch rod, a cooling rate of approximately 10° C. per hour is usually necessary. Cooling rates no greater than 10° C. per hour are preferred. Whatever cooling rate is used, cooling requires careful control in order to limit temperature gradients during cooling. Cooling rapidly, as taught in the prior art, will not provide the desired article.

An additional step is expected to further improve the usefulness of the resulting product. A preliminary heat treatment is applied which subjects the UHMWPE to a temperature approaching, but not reaching, the decomposition point of the UHMWPE, preferably of between 320-355° C. in an inert atmosphere for at least 0.5 hours.

By inert atmosphere in the processes of this invention is meant a vacuum or a gaseous or vaporous environment that is stable and inert to process conditions. Suitable gases include nitrogen and the noble gases. Suitable vapors include those of nonflammable, chemically inert and thermally stable liquids such as the perfluoroalkyl-polyethers (Example 10).

This invention is particularly useful for manufacturing shaped articles where temperature gradients pose a problem during the cooling step, i.e., where the article's cross-sectional dimensions are at least 1 inch × at least 1 inch, usually for joints at least 1 inch × at least 2 inches. Specifically, the importance of this step and of this invention is manifest in producing articles having as its smallest dimension 0.2 inch, i.e., at least 0.2 inch in thickness. It has been found that in such articles, the temperature gradients must still be controlled by the process of this invention in order to obtain the desired product.

In addition to utility in the field of orthopedic replacement, the products are expected to prove useful in other applications also requiring the special properties of the products. Not only shaped articles are of interest, but also films and fibers as well as other "downstream" forms and unshaped granular forms of the products will prove useful. Film to be formed of the product of Example 1 is described in Example 6. These examples are illustrative only, and other forms, shaped and unshaped, of the composition are contemplated within the scope of the invention. Therefore, "article" shall include both shaped articles and unshaped articles.

In the best mode known at this time for using the process of this invention, the gas used in the pressure vessel is argon. Specifically, the shaped article is formed from commercially available UHMWLPE. It is necessary to protect the UHMWLPE from any entry of the gas into the polymer by surrounding the article completely with a thin stainless steel or similar metal can. It should be understood that other gaseous fluids may be used in place of argon. So long as the gas is not affected by the temperatures and pressures used in the process, the gas may be used. Such gases include, but are not lmited to, the noble gases, nitrogen, etc.

In the next step, the protected article is placed in an argon-filled pressure vessel and a pressure of at least 200 MPa is applied with argon and the vessel is heated to about 220° C. for about 6 hours. Thereafter, the temperature is "ramped" down at a rate no greater than about 10° C. per hour to about 160° C. while maintaining the pressure above 280 MPa. The temperature is then "ramped" down at a maximum rate to 50° C. while maintaining the high pressure, after which the pressure is released.

For purposes of this invention, ultrahigh molecular weight linear polyethylene (UHMWLPE) is defined as a linear polyethylene having an estimated weight-average molecular weight in excess of about 400,000, usually 1,000,000 to 10,000,000 as defined by a melt index (ASTMD-1238) of essentially zero and a reduced specific viscosity (RSV) greater than 8, preferably 25-30. The relationships of RSV to intrinsic viscosity and to molecular weight are those developed by R. Chaing as presented by P. S. Francis et al. in J. Polymer Science, 31, 453 (1958).

The improved properties of the products of this process are reflected in a tensile modulus of at least 250 kpsi, a flex modulus of at least 250 kpsi, ultimate tensile strength greater than 4000 kpsi, yield strength greater than 3500 psi and an elongation at break no greater than 500%.

A very important property of the product is its creep resistance. For prosthetic devices, e.g. knee, hip, elbow joints, etc., any substantial creep can be devastating in the loss of the benefits of extremely expensive surgery. Thus, the shaped articles resulting from this invention display as little as a 0.5% loss in thickness when subjected to a compression pressure of 1000 psi for 24 hours at a temperature of 23° C. and a relative humidity of 50% in accordance with ASTM D-621.

Perhaps the most characteristic property of the product is its infrared crystallinity index (IRCI). This property, which provides a reasonably accurate reflection of the crystallinity of this material, is in a range never before attained with any polyethylene materials. To determine this index, samples are first obtained by microforming thin sections. Heat should be avoided during preparation of the samples. IRCI is the ratio of the band at 1894 reciprocal centimeters ($cm^{-1}$) to the band at 1305 reciprocal centimeters ($cm^{-1}$) Since the band at 1894 $cm^{-1}$ is attributed to the crystalline nature of the material and the band at 1305 $cm^{-1}$ is attributed to its amorphous nature, IRCI increases as the crystallinity increases. The product displays an IRCI of at least 0.45. In fact, values of 0.73 and higher have been obtained. On the other hand, IRCI values for prior known UHMWLPE's seldom reach above 0.3.

It should be appreciated that the step of forming the article by milling, casting, or the like from UHMWLPE may be performed as the first step in the process (i.e., before heating or preheating) or as the last step in the process (i.e., after the cooling step).

The invention will be more clearly understood by referring to the drawing and example, which follow. In the drawing, FIG. 1 is a schematic diagram of the equipment used in the process for forming the product of the invention using argon gas.

In the example, most of the properties are measured using standard ASTM tests. All of the physical measurements were carried out under constant humidity (50% relative humidity) and temperature (23° C.) conditions.

Tensile modulus, ultimate tensile strength, yield strength and elongation are measured according to ASTM D-638 with the following modifications:
samples machined into shape without lubricating fluid
type I tensile bar
cross head speed=0.2"/min for tensile modulus 2.0"/min for tensile stress and elongation.

Resistance to deformation (creep) is measured in accordance with ASTM D-621 with the following modifications:
samples machined into cylinders without the use of lubricating fluids
samples measured 0.5"×0.5"×0.5"

Flexural properties are measured according to ASTM D-790 with the following modifications:
samples machined into shape without the use of lubricating fluids
typical flex bar measures 0.125" thick × 0.5" width × 5" length
span or gage is 2.0". (This was determined by a span/depth ratio of 16/1.)
cross head speed=0.05"/min (calculated based on span).

Impact resistance is measured using the notched Izod test given in ASTM D-256 with the following modifications:
samples machined into shape without the use of lubricating fluid
type A or notched IZOD
specimen size is 0.5"×2.5"
0.4" from bottom of vertex to opposite side
1.25" impacted end (from end of bar to vertex of notch)
the notch should be the specified angle of 22.5 degrees.

The following non-limiting examples illustrate the basic principles and unique advantages of the present invention. Various changes and modifications may be made without departing from the spirit and scope of the present invention.

EXAMPLE 1

The material used in this example is American Hoechst 415 GUR ultrahigh molecular weight polyethylene. It was obtained in the form of bars, 3" in diameter and up to 5' long in length. The material will be referred to as UHMWLPE. The molecular weight was over 1,000,000.

One or more pieces of the UHMWLPE 11 were placed into stainless steel, seamless, 48" long cylinders or sleeves 12. The thickness of the stainless steel was ⅛". The bottom of the cylinders was closed by welding a stainless steel cap 13 onto the bottom of the cylinder. The top of the cylinder was partially closed by welding on a modified cap 14 which contained a vacuum port not shown. The cylinder was then evacuated using a vacuum pump and sealed by crimping the port to form a can that surrounds the piece of UHMWLPE completely. The sealed cylinder was then placed in a containment vessel 16 large enough to hold 15 cylinders. The containment vessel 16 was then placed into a hot isostatic pressing (HIP) unit 17 with molybdenum heating units 18. Thermocouples were added to monitor the temperature of the cylinders.

The basic function of the HIP process is to uniformly heat a load while applying pressure uniformly to all surfaces. The pressure medium used in this case was argon. The gas entered at 15 and exited at 19. The UHMWPE is protected from the argon by the stainless steel cans.

The process conditions were:
1. Apply pressure to 39,000 psi (269.1 MPa).
2. Heat to 220° C.
3. Hold for 6 hours at 220° C. and a minimum pressure of 41,000 psi.
4. Ramp temperature down at a rate no faster than 10° C. per hour to 160° C. Pressure is maintained above 41,000 psi (282.9 MPa) during this time.
5. Ramp temperature down at maximum rate to 50° C. while maintaining the pressure above 41,000 psi (282.9 MPa).
6. Below 50° C., pressure may be let down and the cycle ended.

The UHMWPE rods were then removed from the sleeves and parts were fabricated for physical testing. It is noted that the material produced exhibits much higher tensile modulus, flex modulus, melting point, density and creep resistance than the starting material (Control A).

| Material | DSC Melting Point (°C.) | Density (grams/cc) | IRCI |
|---|---|---|---|
| Control A | 137.0-140.7° C. | .93-.94 | 0.24 |
| Example 1 | 148.0-152.0° C. | .947 | ≧0.45 |

| Properties | Control A | Example 1 |
|---|---|---|
| Tensile (ASTM D638) | | |
| Modulus kpsi | 185 | 315 |
| Stress, break, psi | 4500 | 4688 |
| Stress, yield, psi | 3476 | 4082 |
| Elongation, brk, % | 262 | 227 |
| Flexural (ASTM D790) | | |
| Modulus, kpsi | 165 | 291 |
| Deformation (creep) (ASTM D621) | | |
| Load, psi | | |
| 500 | 0.5 | 0.3% |
| 1000 | 1.6 | 0.7 |
| 2000 | 5.9 | 2.4 |

Additional evidence of the products' distinctiveness is found in data produced by small angle X-ray testing A truly characteristic small-angle X-ray scattering plot of desmeared intensity (by the method of P. W. Schmidt, Acta Cryst., 13, 480 (1960) and Acta Cryst., 19, 938 (1965)) (I×(2 theta) squared) versus scattering angle (2 theta) for the material of the invention exhibits two distinct scattering peaks associated with crystal long-spacings in the range of 480 angstroms (at 2 theta=0.184 degrees) and 4610 angstroms (at 2 theta=0.0192 degrees) The presence of the sharp diffraction peak at the lower angle is indicative of an extended polymer chain conformation (with a lamellar thickness greater than 2000 angstroms) whereas the more diffuse higher-angle peak corresponds to a lamellar thickness characteristic of conventional folded chain PE. This provides clear evidence for the presence of two scattering peaks in the subject invention material which correspond to lamellar thicknesses both above and below 2000 angstroms. By comparison, the previously patented extended chain polyethylene of Lupton et al., was reported to exhibit a complete absence of any detectable small angle X-ray scattering in the range of 50 to 2000 angstroms. Consequently this work demonstrates that the subject invention material is morphologically distinguishable from Lupton et al.

EXAMPLE 2

The process described in Example 1 may be modified to yield a product with properties even more suitable for orthopedic replacements than the starting material. It is suggested that the UHMW polyethylene be preliminarily heated to a point closely approaching, but not reaching, the decomposition point of the UHMW polyethylene, preferably between 320–340° C., in an atmosphere of $N_2$ or in a vacuum for six hours. Once so pre-heated, the article is otherwise to be treated as in Example 1.

It is expected that the addition of the preliminary heating step to the process will yield a product displaying improved tensile yield strength, improved elongation (%) at break, and lower creep resistance than the product of Example 1 or the starting material.

EXAMPLE 3

Effect of Sequence of Heat-Treatment, Cooling, Reheating to a Lower Temperature, and Pressure Recrystallization on UHMWPE.

The process described in Example 2 may also be modified to yield a product with properties superior to that found in the starting material. It is suggested that the UHMW polyethylene be preliminarily heated to a point approaching, but not reaching, the decomposition point of the UHMW polyethylene, preferably between 320–340° C., in an atmosphere of $N_2$ or in a vacuum for 5 hours. It is then reheated to approximately 225° C., and pressure recrystallized as in Example 1.

It is expected that the described sequence of preliminary heat treatment, cooling, reheating to a lower temperature, and pressure recrystallization will yield a product displaying improved elongation (%) at break, higher crystallinity index (IR), a higher IZOD impact value, and lower creep resistance than the starting material.

EXAMPLE 4

Effect of Preheating by Refluxing

The process described in Example 3 may be further modified to yield a product with properties superior to that of the starting material and with at least an improved elongation (%) at break as compared to the products yielded by other embodiments of the invention.

It is suggested that a rod approximately 3"×18" of UHMWPE (e.g., Hoechst, Hostalen GUR 415) be preliminarily heated in refluxing vapors of Krytox ®-143AZ (E. I. du Pont de Nemours and Company, Wilmington, Dela.) at approximately 333–335° C. for more than 0.5 hours.

Krytox ®-143AZ is a perfluoroalkylpolyether that is a non-flammable, chemically inert liquid having unusually high thermal and oxidative stability. Other materials demonstrating these characteristics may also be suitable. The refluxing system should be protected by a nitrogen or other inert atmosphere and wrapped with glass insulation to facilitate slow, non-precipitous cooling.

It is expected that the described sequence of preliminary heat treatment by refluxing, cooling, reheating to a lower temperature, and pressure recrystallization will yield a product displaying improved elongation (%) at break, expected to be from 250–900, while retaining a high tensile strength at yield and a high tensile modulus.

EXAMPLE 5

A 3" diameter bar (rod), 18" in length, of American Hoechst Hostalen GUR 415 ultrahigh molecular weight polyethylene, would be heated in an oven and then would be encapsulated with low molecular weight polyethylene by rolling the hot rod onto a sheet of low molecular weight polyethylene heated to 180° C. on a large hot plate. Sheet thickness can be 1/16" or less, provided that the polyethylene is backed by a sheet of impermeable material such as metal foil (e.g., 1-2 mil aluminum foil). If impermeable material is not used, the polyethylene sheet must be sufficiently thick to prevent penetration of the fluid pressure medium. An intervening sheet of "Teflon" Polytetrofluoroethylene film should be kept on the encapsulated rod to prevent sticking to the hot plate. The rod ends are similarly sealed. The "Teflon" film should be kept on the encapsulated rod to prevent sticking in the reactor.

The bar should be heated to 225° C. under a nitrogen atmosphere and transfered to the reactor at 225° C. After sealing, the reactor pressure is taken to 300 MPa which should cause the temperature to reach 237° C. The reactor should be permitted to cool to 180° C. in 6.5 h, then maintained at this temperature for 1 h. The temperature is dropped to 170° C., held at this temperature for 3h, then should be cooled slowly to 150° C. from where it is cooled rapidly.

The rod, which remains coated, should be cut and machined into two test pieces (A and B) which should give results showing improved properties. For example, one would expect to find at 1st Heat a melting point, °C., in the range of 149 to 155 and a heat of fusion, J/g, in the range of 200.0 to 220.0. At 2nd heat melting point, °C., is expected in the range of 130 to 140.0 with a heat of fusion, J/g, expected in the range of 140.0 to 146. At crystallinity index (IR) of approximately 0.57, the tensile strength of the material (psi) at yield is expected in the range of 4000 to 4500, at maximum is expected in the range of 7000 to 9000, and at break is expected in the range of 7000 to 9000. Elongation, % at break, is expected in the range of 320 to 350. Modulus, kpsi, is expected in the range of 350 to 365.0. Creep Deformation, % measured by ASTM D621, is expected to be approximately 0.6. The IZOD Impact (ftlb/in. of notch) is expected to be in the range of 15.5 to 16.0.

EXAMPLE 6

A 5.75" segment of enhanced ultrahigh molecular weight polyethylene prepared as in Example 1, should be skived to two films (A and B), of 11 mil and 5 mil thickness, respectively. The following properties may be expected.

The tensile strength of the material (psi) at yield is expected to range from 3000 to 3200, at maximum is expected to range from 4000 to 7000, at break is expected to range from 4000 to 7000, and at 5% elongation is expected to be 2500 to 2800. The tensile modulus (kpsi) is expected ro range from 125.0 to 200.0. The elongation at break (%) is expected to range from 200 to 500.

The skived films could be hot drawn in a tenter frame at 140° C. If one piece of the 5 mil film is drawn 6 fold in one direction the results could be tensile strength (psi) at yield that is approximately 37,820, at maximum that is approximately 42,100, at break that is approximately 46,400. Tensile modulus (kpsi) could be approximately 93. Elongation at break (%) could be approximately 56 with a thickness in mils of 2.6.

If a second piece of the 5 mil film could be drawn 3 fold in both directions the results could be tensile strength (psi) at yield that is approximately 13,800, at maximum that is approximately 19,400, at break that is approximately 19,000. Tensile modulus (kpsi) could be approximately 95.0. Elongation at break (%) could be approximately 132 with a thickness in mils of 1.6.

What is claimed is:

1. A process for obtaining a shaped article of an ultrahigh molecular weight linear polyethylene exhibiting a flexural modulus of 250,000–500,000 psi, a tensile stress at yield of 3500–4500 psi, a tensile stress at break of 4000–9000 psi, a tensile modulus of 250,000–700,000 psi, an elongation of 200–500%, a notched Izod impact resistance of 12–25 ft. lb. per inch of notch, a creep at a compression of 1000 psi of less than 1% after 24 hours at a temperature of 23° C. and a relative humidity of 50%, the polyethylene having a molecular weight of 400,000–10,000,000, a single crystalline melting point of greater than 144° C., the reduction in said melting point upon remelting being greater than 11° C. and an infrared crystallinity index of at least about 0.45 consisting essentially of the following steps:
   (a) forming said article of an ultrahigh molecular weight linear polyethylene having a molecular weight of 400,000–10,000,000;
   (b) surrounding said article with an inert material that is collapsible and impermeable;
   (c) subjecting said surrounded article to a gas under pressure of at least 280 MPa and a temperature of 190° C.–300° C.;
   (d) maintaining the temperature from 190° C.–300° C. and the pressure of at least 280 MPa for at least 0.5 hour;
   (e) reducing the temperature to below 160° C.–170° C., while maintaining the pressure at at least 280 MPa, the rate of reduction in temperature being such that temperature gradients in the shaped article are substantially avoided; and
   (f) cooling to a temperature of about 130° C. or below and releasing the pressure to approximately 100 kPa in a manner such that remelting of said article is prevented.

2. The process of claim 1, including subjecting said article before step (c) to heat treatment at an elevated temperature not exceeding the decomposition point of the article, in an inert atmosphere for at least 0.5 hour.

3. The process of claim 2 wherein said heat treatment before step (c) is accomplished by reflux vapors.

4. The process of claim 1 wherein said article is enclosed within a stainless steel material that prevents said gas from contacting the surfaces of said article.

5. The process of claim 4 wherein said gas is argon.

6. The process of claim 5 wherein said pressure in step (c) is at least 300 MPa.

7. The process of claim 5 wherein said temperature in step (c) is 190° C.–230° C.

8. The process of claim 5 wherein the temperature and pressure in step (f) is maintained for at least one hour.

9. The process of claim 1 wherein step (a) is performed after step (f) is performed.

10. The process of claim 2 wherein said heat treatment is at a temperature not exceeding 355° C.

11. The process of claim 10 wherein said heat treatment is at a temperature in the range of 320°–355° C.

12. An ultrahigh molecular weight linear polyethylene exhibiting a flexural modulus of 250,000–500,000 psi, a tensile stress at yield of 3500–4500 psi, a tensile stress at break of 4000–9000 psi, a tensile modulus of 250,000–700,000 psi, a notched Izod impact resistance of 12–25 ft. lb. per inch of notch, a creep at a compression of 1000 psi of less than 1% after 24 hours at a temperature of 23° C. and a relative humidity of 50%, the polyethylene having a molecular weight of 400,000–10,000,000, a single crystalline melting point of greater than 144° C., the reduction in said melting point upon remelting being greater than 11° C. and an infrared crystallinity index of at least about 0.45 formed by the process consisting essentially of the following steps:
   (a) forming an article of an ultrahigh molecular weight linear polyethylene having a molecular weight of 400,000–10,000,000;
   (b) surrounding said article with an inert material that is collapsible and impermeable;
   (c) subjecting said surrounded article to a gas under pressure of at least 280 MPa and a temperature of 190° C.–300° C.;
   (d) maintaining the temperature from 190° C.–300° C. and the pressure of at least 280 MPa for at least 0.5 hour;
   (e) reducing the temperature to below 160° C.–170° C., while maintaining the pressure at at least 280 MPa, the rate of reduction in temperature being such that temperature gradients in the shaped article are substantially avoided; and
   (f) cooling to a temperature of about 130° C. or below and releasing the pressure to approximately 100 kPa in a manner such that remelting of said article is prevented.

13. The product by the process of claim 12 which is subjected before step (c) to heat treatment at an elevated temperature not exceeding the decomposition point of the article, in an inert atmosphere for at least 0.5 hour.

14. The product by the process of claim 13 which is subjected to said heat treatment before step (c) by means of refluxing vapors.

15. The product by the process of claim 12 which is enclosed within a stainless steel material that prevents said gas from contacting the surfaces of said article.

16. The product by process of claim 15 which is produced with the use of argon.

17. The product by process of claim 16 which is subjected in step (b) to pressure of at least 300 MPa.

18. The product by process of claim 16 which is subjected in step (c) to temperatures in the range of 190° C.–230° C.

19. The product by process of claim 16 which is subjected in step (f) to temperatures and pressures maintained for at least one hour.

20. The product by process of claim 12 which is produced when step (a) is performed after step (f) is performed.

21. The product of the process of claim 13 which is subjected before step (c) to said heat treatment at a temperature not exceeding 355° C.

22. The product of the process of claim 21 which is subjected before step (c) to said heat treatment at a temperature in the range of 280°-355° C.

23. The polyethylene of claim 12 in the form of a film.

24. The polyethylene of claim 13 in the form of a film.

25. The polyethylene of claim 12 in the form of a fiber.

26. The polyethylene of claim 13 in the form of a fiber.

* * * * *